United States Patent
Zhang et al.

(10) Patent No.: US 10,401,308 B2
(45) Date of Patent: Sep. 3, 2019

(54) DUAL-ENERGY DETECTION APPARATUS, SYSTEM AND METHOD

(71) Applicant: Nuctech Company Limited, Beijing (CN)

(72) Inventors: Qingjun Zhang, Beijing (CN); Yuanjing Li, Beijing (CN); Shuwei Li, Beijing (CN); Ziran Zhao, Beijing (CN); Weibin Zhu, Beijing (CN); Junxiao Wang, Beijing (CN); Jianhua Li, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 216 days.

(21) Appl. No.: 15/278,470

(22) Filed: Sep. 28, 2016

(65) Prior Publication Data
US 2017/0184515 A1 Jun. 29, 2017

(30) Foreign Application Priority Data
Dec. 29, 2015 (CN) .......................... 2015 1 1017642

(51) Int. Cl.
*G01T 1/20* (2006.01)
*G01N 23/087* (2018.01)

(52) U.S. Cl.
CPC .......... *G01N 23/087* (2013.01); *G01T 1/2008* (2013.01); *G01T 1/2018* (2013.01);
(Continued)

(58) Field of Classification Search
CPC ........... G01N 23/087; G01N 2223/202; G01N 2223/501; G01N 2223/505; G01T 1/2008; G01T 1/2018
(Continued)

(56) References Cited

U.S. PATENT DOCUMENTS

| 4,963,746 A * | 10/1990 | Morgan | ................... A61B 6/06 250/363.02 |
| 2007/0114426 A1 * | 5/2007 | Tkaczyk | ............... G01T 1/2018 250/370.09 |
| 2012/0025086 A1 | 2/2012 | Takihi | |

FOREIGN PATENT DOCUMENTS

| CN | 101937094 A | 1/2011 |
| CN | 202948145 U | 5/2013 |

(Continued)

OTHER PUBLICATIONS

Great Britain Search and Examination Report dated Mar. 17, 2017 received in British Patent Application No. GB 1616620.9.
(Continued)

*Primary Examiner* — Courtney D Thomas
(74) *Attorney, Agent, or Firm* — Scully, Scott, Murphy & Presser, P.C.

(57) ABSTRACT

The present application relates to a dual-energy detection method, system and apparatus. The apparatus includes: a first pixel detector array proximal to a ray source, configured to detect ray source photons having relatively low energy; and a second pixel detector array distal from the ray source, configured to detect ray source photons having relatively high energy; wherein the first pixel detector array includes a plurality of rows of first pixel detectors, the first pixel detector including a first sensitive medium, a first photosensitive device, a first incidence plane, and a first window; the second pixel detector array includes a single row of second pixel detectors, the second pixel detector including a second sensitive medium, a second photosensitive device, a second incidence plane, and a second window; and each of the second pixel detectors has the same pixel area as corresponding plurality of first pixel detectors thereof.

14 Claims, 5 Drawing Sheets

(52) U.S. Cl.
CPC . *G01N 2223/202* (2013.01); *G01N 2223/501* (2013.01); *G01N 2223/505* (2013.01)

(58) Field of Classification Search
USPC ............. 378/98.8, 98.9; 250/370.08, 370.09, 250/370.11
See application file for complete search history.

(56) References Cited

FOREIGN PATENT DOCUMENTS

| DE | 102011089595 A1 | 6/2013 |
|----|-----------------|--------|
| EP | 2 400 318 A1 | 12/2011 |
| JP | 2010276409 A | 12/2010 |
| WO | 2013/054300 A2 | 4/2013 |

OTHER PUBLICATIONS

"Energy Dispersive X-Ray Fluorescence Method", pp. 127 (Apr. 30, 1994), together with an English-language abstract.

"Airport Security Precaution Technology", pp. 68 (Apr. 30, 2013), together with an English-language abstract.

"X-Ray Visual Automatic Detection Technology and Application", pp. 60-64 (Nov. 30, 2012), together with an English-language abstract.

"Research of y Ray Detection System Based on PIN Photodiode", pp. 40-41 (Aug. 15, 2006), together with an English-language abstract.

Xu, X, et al. "Electrical and Electronic Technology, Chapter 8 Common Semiconductor Device" "Twelfth Five-Tear Plan" Planned Textbook of Electrician & Electron Foundation Course for General Higher Education (Sep. 1, 2015), with English translation (total 7 pages).

* cited by examiner

DUAL-ENERGY DETECTION APPARATUS, SYSTEM AND METHOD

TECHNICAL FIELD

The present disclosure relates to the field of radiation detection technologies, and in particular, to a dual-energy detection apparatus, system and method.

BACKGROUND

In a megavolt-level X-ray detection system, improving the effective atomic number identification capability for a substance and enhancing space identification capability are two important aspects to be developed.

Therefore, new dual-energy detection apparatus, system and method are desired.

The above information disclosed in the background portion is only used to reinforce understanding of the background of the present disclosure. Therefore, the above information may include information that is not prior arts known to persons of ordinary skill in the art.

SUMMARY

The present disclosure provides a dual-energy detection apparatus, system and method, which are capable of enhancing capability of identifying an object and improving space identification indicators.

Other characteristics, features, and advantages of the present disclosure will become apparent through the following detailed description, or will be partially learned from practice of the present disclosure.

According to one aspect of the present disclosure, a dual-energy detection apparatus is provided. The apparatus includes: a first pixel detector array proximal to a ray source, configured to detect ray source photons having relatively low energy; and a second pixel detector array distal from the ray source, configured to detect the ray source photons having relatively high energy which have passed through the first pixel detector array. The first pixel detector array includes a plurality of rows of first pixel detectors, the first pixel detector including a first sensitive medium, a first photosensitive device, a first incidence plane for incidence of the ray source, and a first window coupled to the first photosensitive device, the first incidence plane facing towards the ray source; the second pixel detector array includes a single row of second pixel detectors, the second pixel detector including a second sensitive medium, a second photosensitive device, a second incidence plane for incidence of the ray source, and a second window coupled to the second photosensitive device; and each of the second pixel detectors has the same pixel area as corresponding plurality of first pixel detectors thereof.

According to an embodiment of the present disclosure, the first sensitive medium is a first scintillator; each of the first pixel detectors includes the first scintillator having a rectangular shape and a first reflection layer coating the first scintillator, the first reflection layer exposing the first window; and one side of each of the first pixel detectors opposite to the first window is the first incidence plane.

According to an embodiment of the present disclosure, the second sensitive medium is a second scintillator; and each of the second pixel detectors includes the second scintillator having a rectangular shape and a second reflection layer coating the second scintillator, the second reflection layer exposing the second window.

According to an embodiment of the present disclosure, the first pixel detector further includes a first data collection board.

According to an embodiment of the present disclosure, the second pixel detector further includes a second data collection board.

According to an embodiment of the present disclosure, the ray source includes an X-ray source and an isotopic source.

According to an embodiment of the present disclosure, a mass thickness of the first pixel detector is determined based on any one or any combination of the type of the ray source, the type of the first sensitive medium and the size of the pixel.

According to an embodiment of the present disclosure, a mass thickness of the second pixel detector is selected such that the second pixel detector array is capable of effectively detecting the ray source photons having relatively high energy, and the mass thickness of the second pixel detector is greater than the mass thickness of the first pixel detector.

According to another aspect of the present disclosure, a dual-energy detection system is provided. The system includes: a ray source located on one side of a to-be-detected object; and a dual-energy detection apparatus located on the other side of the to-be-detected object. The dual-energy detection apparatus includes: a first pixel detector array proximal to the ray source, configured to detect ray source photons having relatively low energy; a second pixel detector array distal from the ray source, configured to detect the ray source photons having relatively high energy which have passed through the first pixel detector array. The first pixel detector array includes a plurality of rows of first pixel detectors, the first pixel detector including a first sensitive medium, a first photosensitive device, a first incidence plane for incidence of the ray source, and a first window coupled to the first photosensitive device, the first incidence plane facing towards the ray source; the second pixel detector array includes a single row of second pixel detectors, the second pixel detector including a second sensitive medium, a second photosensitive device, a second incidence plane for incidence of the ray source, and a second window coupled to the second photosensitive device; and each of the second pixel detectors has the same pixel area as corresponding plurality of first pixel detectors thereof.

According to an embodiment of the present disclosure, the first pixel detector further includes a first data collection board.

According to an embodiment of the present disclosure, the second pixel detector further includes a second data collection board.

According to an embodiment of the present disclosure, the system further includes a processing apparatus, wherein the processing apparatus is respectively connected to the first data collection board and the second data collection board, reads output signals of the first pixel detector array and the second pixel detector array, and acquires effective atomic number information of the to-be-detected object based on the output signals.

According to an embodiment of the present disclosure, the ray source includes an X-ray source and an isotopic source.

According to still another aspect of the present disclosure, a dual-energy detection method is provided. The method includes: arranging a first pixel detector array proximal to a ray source, which is configured to detect ray source photons having relatively low energy, wherein the first pixel detector array includes a plurality of rows of first pixel detectors, the first pixel detector including a first scintillator, a first photosensitive device, a first incidence plane for incidence of the ray source, and a first window coupled to the first photosensitive device, the first incidence plane facing towards the ray source; arranging a second pixel detector array distal from the ray source, which is configured to detect the ray source photons having relatively high energy which have passed through the first pixel detector array, wherein the second pixel detector array includes a single row of second pixel detectors, the second pixel detector including a second scintillator, a second photosensitive device, a second incidence plane for incidence of the ray source, and a second window coupled to the second photosensitive device, each of the second pixel detectors having the same pixel area as corresponding plurality of first pixel detectors thereof; and irradiating the first pixel detector array from the first incidence plane by using the ray source.

According to an embodiment of the present disclosure, the method further includes: reading output signals of the first pixel detector array and the second pixel detector array; and acquiring effective atomic number information of a to-be-detected object based on the output signals.

With the dual-energy detection apparatus, system and method according to the present disclosure, capability of identifying an object is enhanced and meanwhile space identification indicators are improved.

It shall be appreciated that the above general description and the detailed description hereinafter are only illustrative but not for limiting the present disclosure.

BRIEF DESCRIPTION OF THE DRAWINGS

Exemplary embodiments of the present disclosure will be described in detail with reference to the accompanying drawings, such that the above and other features and advantages of the present disclosure will become more apparent.

DETAILED DESCRIPTION

Exemplary embodiments of the present disclosure are hereinafter described more fully with reference to the accompany drawings. However, the exemplary embodiments may be implemented in a plurality of manners, and shall not be construed as being limited to the implementations described herein. Instead, such exemplary embodiments are provided to more thoroughly and completely illustrate the present disclosure, and fully convey the concepts of the exemplary embodiments to persons skilled in the art. In the drawings, like reference numerals denote like or similar structures or elements. Therefore, repetitive descriptions thereof are not given any further.

In addition, the described characteristics, structures, or features may be incorporated in one or more embodiments in any suitable manner. In the description hereinafter, more details are provided such that sufficient understanding of the embodiments of the present disclosure may be achieved. However, a person skilled in the art would be aware that the technical solutions of the present disclosure may be practiced without one or more of the specific details, or may be practiced using other methods, components, materials, apparatuses, steps or the like. Under other circumstances, commonly known structures, methods, apparatuses, practices, materials or operations are not illustrated or described in detail to avoid various aspects of the present disclosure from becoming ambiguous.

The block diagrams illustrated in the drawings are merely functional entities, but are not necessarily physically independent entities. That is, these functional entities may be implemented by means of software, or these functional entities or a portion of these functional entities may be implemented in one or a plurality of software hardened modules, or these functional entities may be implemented in different networks and/or processor apparatuses and/or microcontroller apparatuses.

Figure 1:
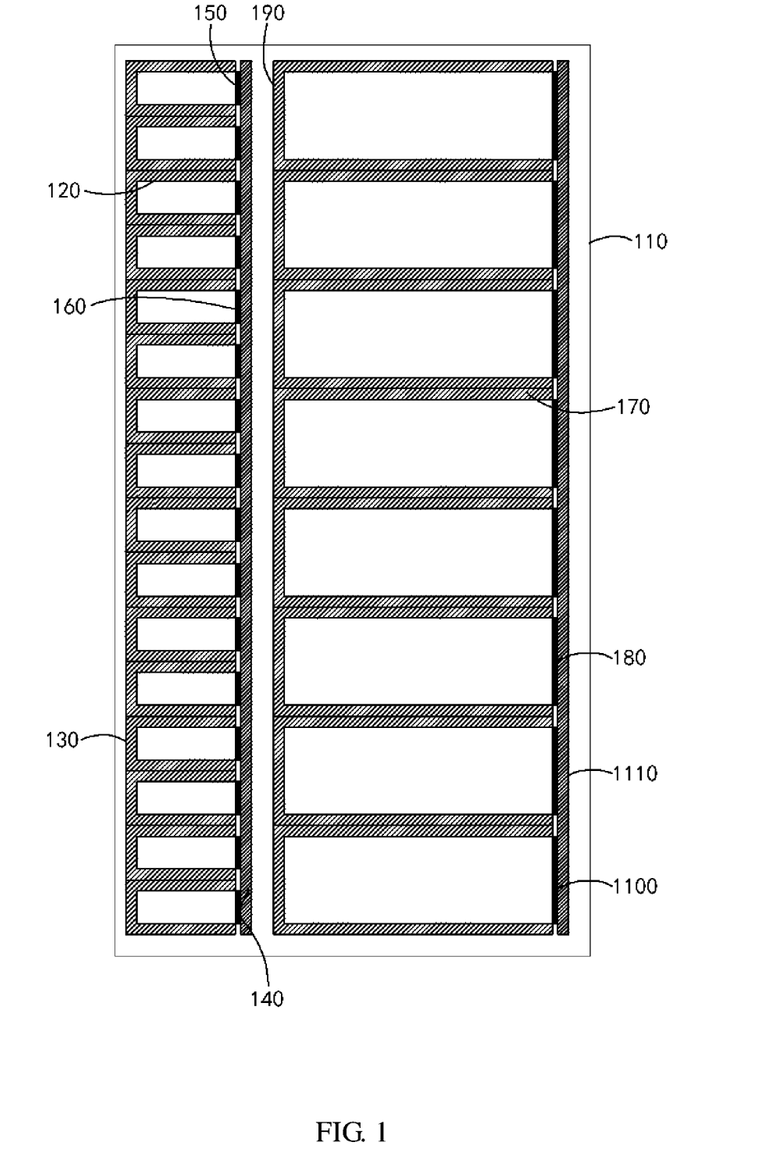
FIG. 1 schematically illustrates a structural diagram of a dual-energy detection apparatus according to an exemplary embodiment of the present disclosure.

FIG. 1 schematically illustrates a structural diagram of a dual-energy detection apparatus 110 according to an exemplary embodiment of the present disclosure.

As illustrated in FIG. 1, the apparatus 110 includes: a first pixel detector array 120 proximal to the ray source, configured to detect ray source photons having relatively low energy; a second pixel detector array 170 distal from the ray source, configured to detect the ray source photons having relatively high energy which have passed through the first pixel detector array 120. The first pixel detector array 120 includes a plurality of rows of first pixel detectors, the first pixel detector including a first sensitive medium, a first photosensitive device 150, a first incidence plane 130 for incidence of the ray source, and a first window 140 coupled to the first photosensitive device 150, the first incidence plane 130 facing towards the ray source; the second pixel detector array 170 includes a single row of second pixel detectors, the second pixel detector including a second sensitive medium, a second photosensitive device 1100, a second incidence plane 190 for incidence of the ray source, and a second window 180 coupled to the second photosensitive device 1100; and each of the second pixel detectors has the same pixel area as corresponding plurality of first pixel detectors thereof.

According to an exemplary embodiment, the first pixel detector is a small-pixel detector or a low-energy detector, the second pixel detector is a large-pixel detector or a high-energy detector, wherein the terms "large pixel", "small pixel", "high energy" and "low energy" are relatively defined. For example, the small pixel may be defined by comparison of the lateral size (that is, the size in a direction perpendicular to the incidence direction of the ray) of the first pixel detector and a secondary electron range, and when the lateral size and the secondary electron range are substantially equivalent to each other, it may be considered that the first detector is the small-pixel detector. The small pixel may also be determined by comparison of the lateral size of the first pixel detector and the length of the first sensitive medium (for example, a scintillator). When the lateral size of the first pixel detector is less than the length of the first sensitive medium by a numerical level, for example, when the length of the first sensitive medium is 30 mm, and the lateral size of the first pixel detector is less than 3 mm, it may be considered that the first pixel detector is the small-pixel detector. Likewise, the large pixel may be determined by comparison of the lateral size of the second pixel detector and the secondary electron range, or by comparison of the lateral size of the second pixel detector and the length of the second sensitive medium. For example, when the lateral size of the second pixel detector and the length of the second sensitive medium are in the same numerical level or the lateral size of the second pixel detector is over 20% of the length of the second sensitive medium, it may be considered that the second pixel detector is the large-pixel detector. Nevertheless, the small-pixel detector and the large-pixel detector may be selected according to the application scenario, which is not limited in the present disclosure.

According to an exemplary embodiment, depending on the specific system settings, for example, the pixel detector mainly detecting X-ray photons lower than 2 megavolts is referred to as a low-energy detector, and the pixel detector mainly detecting X-ray photons higher than 2 megavolts is referred to as a high-energy detector. Nevertheless, the low-energy detector and the high-energy detector may be selected according to the application scenario, which is not limited in the present disclosure.

FIG. 1 is a sectional view of a dual-energy detection apparatus along an incidence direction of an X-ray according to the present disclosure. A low-energy small-pixel detector array is located proximal to an X-ray source, the X-ray is perpendicular to a sensitive plane (that is, the first incidence plane) and is incident to the detection apparatus, the first photosensitive device is arranged on the first window facing directly to the first incident plane of each low-energy small-pixel detector channel, and signals output by the first photosensitive device are transmitted to the first data collection board. A high-energy large-pixel detector array is located at the rear of the low-energy small-pixel detector array, and a second photosensitive device is coupled to one surface of the high-energy large-pixel detector array, wherein signals output by the second photosensitive device are transmitted to the second data collection board. In the drawings, a high-energy large-pixel detector corresponds to 2×4 low-energy small-pixel detectors located in front, and they have the same pixel area.

According to an exemplary embodiment, the first sensitive medium is a first scintillator; each of the first pixel detectors includes the first scintillator having a rectangular shape and a first reflection layer coating the first scintillator, the first reflection layer exposing the first window; and one side of each of the first pixel detectors opposite to the first window is the first incidence plane.

According to an exemplary embodiment, the second sensitive medium is a second scintillator; and each of the second pixel detectors includes the second scintillator having a rectangular shape and a second reflection layer coating the second scintillator, the second reflection layer exposing the second window. One side of each of the second pixel detectors opposite to the second window is the second incidence plane.

In the current radiation detection field, the core constitutional part of a radiation detection system is the detector array, which directly determines the performance indicator of the entire system. Generally, a radiation detection system needs hundreds of detection units to tens of thousands of detection units (in radiation imaging, the detection units are pixels), and each detection unit has a sensitive surface having a size from 1 mm to tens of millimeters. At present, the scintillator detector is the mainstream detector in radiation imaging, and a scintillator detector includes a plurality of scintillator units (that is, the first scintillator and the second scintillator). For convenience of production, generally a plurality of scintillator units are fixed to form a row or several rows for production and installation. Such a scintillator detector is mainly composed of a scintillator (that is, the sensitive medium) with the periphery being a reflection layer, and a photosensitive device.

At present, in a megavolt-level X-ray radiation detection system, a dual-energy X-ray beam method is mainly employed to implement measurement of effective atomic number information of the substance, that is, implementing the measurement by alternately producing two groups of X-ray beams with different energies. However, with this method, on one hand, a time difference may be present between the two X-ray beams, that is, a position deviation is present with respect to the to-be-detected object, and therefore the precision of substance identification is restricted; on the other hand, in the practical product, generally a dual-energy electron accelerator is used as the X-ray source, and this method imposes higher requirements on the stability of the output energy and ray strength, and thus the technical complexity is high.

With respect to the improvement of the space identification indicator in the megavolt-level X-ray detection system, the main method is to use small-pixel detectors. However, the small-pixel detectors are subject to limitations in the megavolt-level system. To ensure the detection speed, with respect to the small-pixel detectors, an array of a plurality of rows of small-pixel detectors is generally used. Such a structure of the array of the plurality of rows of small-pixel detectors requires that the photosensitive device of the scintillator detector be arranged on a side of the scintillator which is reverse to the side facing the radiation of the ray beam. However, to ensure a sufficient detection efficiency, the size (i.e., the mass thickness of the first pixel detector) of the scintillator along the incidence direction of the ray beam needs to be larger, and the scintillation light needs to be reflected for multiple times before it is collected. As a result, the collection efficiency of the scintillation light is reduced, such that the amplitude and signal-to-noise ratio of the output signals are affected and finally the penetration indicator is affected. In addition, the crosstalk between the detectors is increased, and thus the space identification indicator is affected. In addition, the increase in the mass thickness of the small-pixel detectors also imposes higher requirements on the manufacture process, and thus difficulty is caused during implementation. Herein, the "mass thickness" refers to the product of the average density of the substance along the thickness direction and the thickness of the substance (with the unit of $g/cm^2$).

According to an exemplary embodiment, the first pixel detector further includes a first data collection board 160.

According to an exemplary embodiment, the second pixel detector further includes a second data collection board 1110.

According to an exemplary embodiment, the ray source includes an X-ray source and an isotopic source.

According to an exemplary embodiment, a mass thickness of the first pixel detector is determined based on any one or any combination of the type of the ray source, the type of the first sensitive medium and the size of the pixel.

According to an exemplary embodiment, a mass thickness of the second pixel detector is selected such that the second pixel detector array is capable of effectively detecting the ray source photons having relatively high energy, and the mass thickness of the second pixel detector is greater than the mass thickness of the first pixel detector.

According to an exemplary embodiment, the dual-energy detection apparatus may also be applied to a dual-energy X-ray beam system, wherein two groups of high-energy and low-energy detectors, and high-energy and low-energy X-ray beams produce higher effective atomic number information that may be used to analyze the to-be-detected object. Therefore, an effect of improving the substance identification capability is achieved.

The small-pixel detector arranged at the front has a good space identification capability. When the to-be-detected object is relatively thick, in practice, the focus is the penetration, and signals output by the low-energy small-pixel detector arranged at the front and output by the high-energy large-pixel detector arranged at the rear are combined. Therefore, the penetration indicator is improved.

According to an exemplary embodiment, with respect to the pixel size, mass thickness (that is, the size along the incidence direction of the ray), material and the like parameters of the small-pixel detector, and the parameters of the large-pixel detector arranged at the rear, an optimal solution may be determined based on the practical calculation and experiment of the system. If the mass thickness is too small, it is hard to ensure that sufficient relative low-energy X-ray photons can be detected; and if the mass thickness is too large, it may result in that more X-ray photons with high energy are detected, thereby affecting signal outputs from the large-pixel detector arranged at the rear. For example, the mass thickness of the small-pixel detector may be selected as 4 mm, and the mass thickness of the large-pixel detector may be selected as 30 mm, which are not limited in the present disclosure.

The dual-energy detection apparatus according to the present disclosure includes a plurality of rows of low-energy small-pixel detectors proximal to the ray source and a single row of high-energy large-pixel detectors distal from the ray source, which may be applied to a megavolt-level X-ray detection system, and is capable of improving both the substance identification capability and the space identification indicator, providing the function of dual-energy substance identification, and providing higher space resolution, higher detection efficiency and higher sensitivity.

Figure 2:
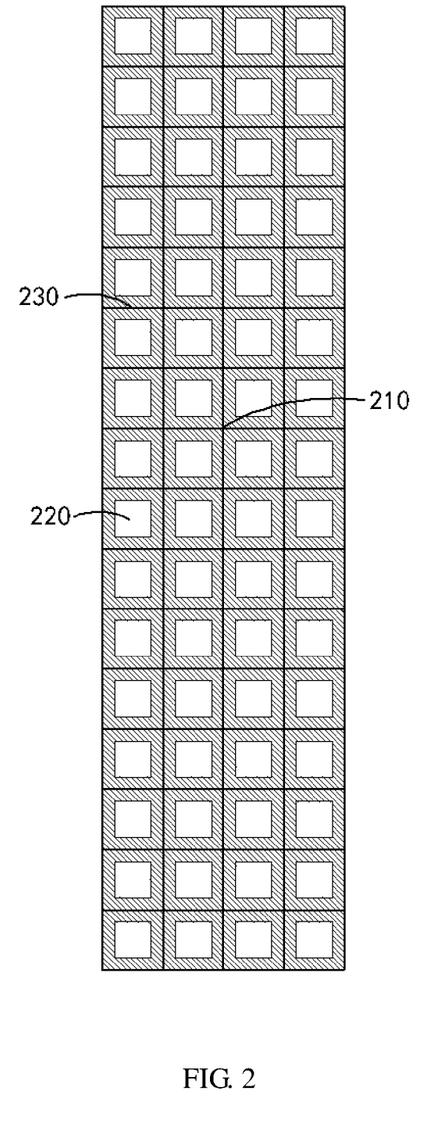
FIG. 2 schematically illustrates a structural diagram of an array of a plurality of rows of first pixel detectors according to an exemplary embodiment of the present disclosure.

FIG. 2 schematically illustrates a structural diagram of an array of a plurality of rows of first pixel detectors according to an exemplary embodiment of the present disclosure.

As illustrated in FIG. 2, it is a sectional view illustrating an array 210 of a plurality of rows of first pixel detectors (for example, small-pixel detectors) in a direction perpendicular to the incidence direction of X-rays. A plurality of low-energy small-pixel detectors form a 4×16 first pixel detector array, wherein each of the first pixel detectors is constituted by a first sensitive medium 220 formed of a scintillator and a first reflection layer 230 coating the scintillator. Specifically, the two-dimensional arrangement number of the small-pixel detectors may be selected according to the application scenario, which is not limited to the arrangement illustrated in FIG. 2.

Figure 3:
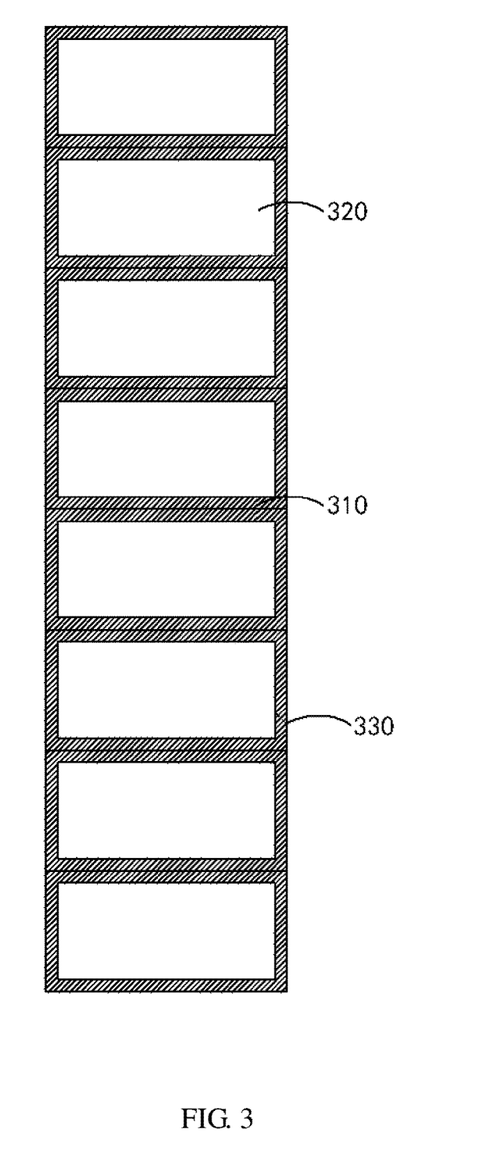
FIG. 3 schematically illustrates a structural diagram of an array of a single row of second pixel detectors according to an exemplary embodiment of the present disclosure.

FIG. 3 schematically illustrates a structural diagram of an array of a single row of second pixel detectors according to an exemplary embodiment of the present disclosure.

As illustrated in FIG. 3, it is a sectional view illustrating an array 310 of a single row of second pixel detectors (for example, large-pixel detectors) in a direction perpendicular to the incidence direction of X-rays. High-energy large-pixel detectors on eight channels form the second pixel detector array. Each of the high-energy large-pixel detectors is also constituted by a second sensitive medium 320 formed of a scintillator and a second reflection layer 330 coating the scintillator.

The bremsstrahlung radiation X-ray energy spectrum produced by an electron accelerator (which may be a single-energy, dual-energy or multi-energy electron accelerator) is a contiguous energy spectrum, and energy distribution of the X-ray photons ranges from 0 to the energy of the electron beam. Approximately, the higher the X-ray photon energy is, the smaller the half-value layer is, i.e., the stronger the penetration is. With respect to the to-be-detected substance, the proportions of the absorbed X-ray photons with different energies are different depending on the effective atomic number of the substance. The small-pixel detector, due to restriction of the mass thickness, is suitable for being arranged at the front and detecting X-ray photons having relatively low energy, and the high-energy detector arranged at the rear may detect more X-ray photons having relatively high energy. By parsing the output signals of the two detectors, the effective atomic number information of the to-be-detected substance may be obtained. As such, the energy response difference to high energy and low energy is inhered in the apparatus according to the present disclosure, and the operation of the apparatus is more stable; and high-energy signals and low-energy signals are produced from the X-ray beam at the same time point, with no deviation in terms of time and position.

Figure 4:
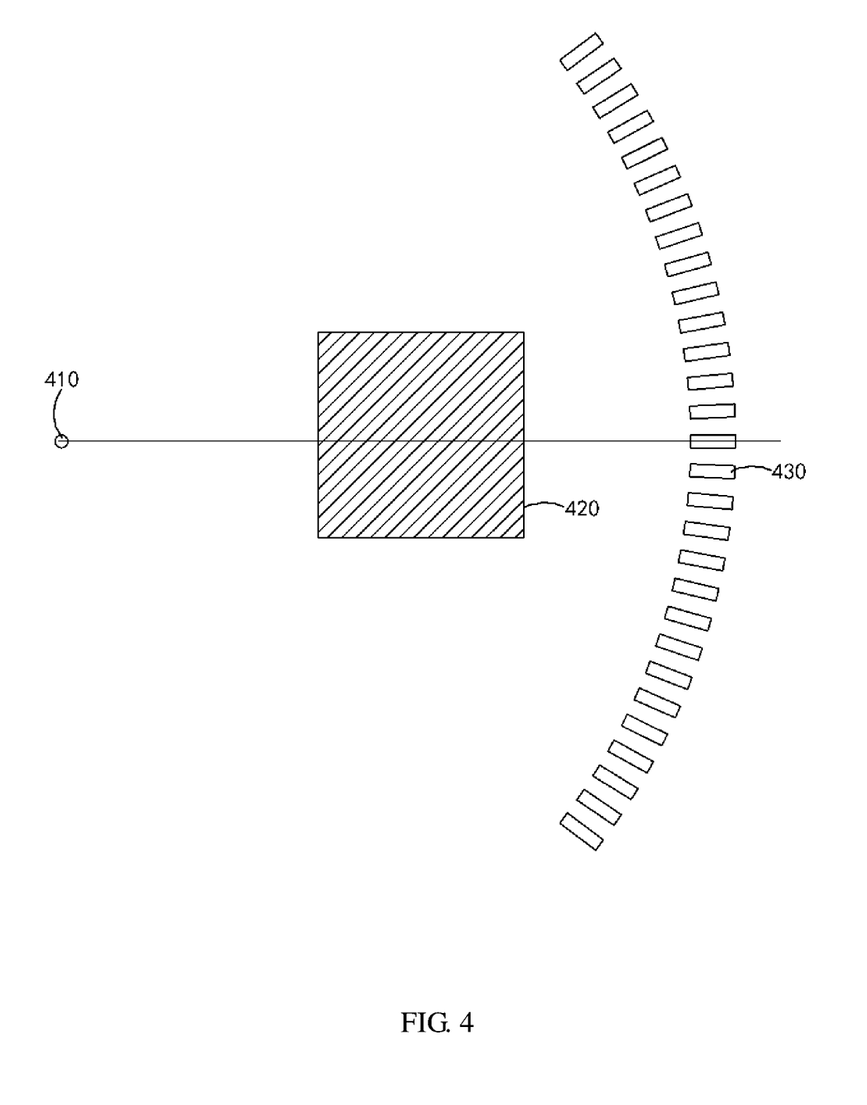
FIG. 4 schematically illustrates a structural diagram of a dual-energy detection system according to an exemplary embodiment of the present disclosure.

FIG. 4 schematically illustrates a structural diagram of a dual-energy detection system according to an exemplary embodiment of the present disclosure.

As illustrated in FIG. 4, the system includes: a ray source 410 located on one side of a to-be-detected object 420; and a dual-energy detection apparatus 430 located on the other side of the to-be-detected object 420.

The dual-energy detection apparatus 430 includes: a first pixel detector array proximal to the ray source 410, configured to detect ray source photons having relatively low energy; and a second pixel detector array distal from the ray source 410, configured to detect the ray source photons having relatively high energy which have passed through the first pixel detector array.

The first pixel detector array includes a plurality of rows of first pixel detectors, the first pixel detector including a first sensitive medium, a first photosensitive device, a first incidence plane for incidence of the ray source 410, and a first window coupled to the first photosensitive device, the first incidence plane facing towards the ray source 410; the second pixel detector array includes a single row of second pixel detectors, the second pixel detector including a second sensitive medium, a second photosensitive device, a second incidence plane for incidence of the ray source, and a second window coupled to the second photosensitive device; and each of the second pixel detectors has the same pixel area as corresponding plurality of first pixel detectors thereof.

According to an exemplary embodiment, the mass thickness of a plurality of rows of small-size small-pixel detectors may be determined based on an optimal substance identification effect according to the factors in the specific system, for example, the type of the electron accelerator employed, the type of the sensitive medium, the pixel size and the like. The plurality of rows of small-size small-pixel detectors are configured to detect the X-ray photons having relatively low energy.

According to an exemplary embodiment, a detector module arc array formed of the dual-energy detection apparatus 430 and the ray source (for example, the X-ray source) are respectively arranged on two sides of the to-be-detected object 420. The sensitive plane of each detector faces directly towards the X-ray source 410.

The module may implement, in a radiation detection system employing the single-energy electron accelerator, effective atomic number identification of the substance. In addition, the module may improve, in a radiation detection system employing the dual-energy or multi-energy X-ray, the substance identification capability.

By combination of the small-pixel detectors and the large-pixel detectors, the space identification and the penetration indicator are both improved.

According to an exemplary embodiment, the mass thickness of the large-pixel detector arranged at the rear is sufficient to ensure that the detector detects most of the X-ray photons that have passed through the small-pixel detector array. These X-ray photons have relatively high energy. In addition, the pixel size of a large-pixel detector is the same as the total pixel size of the corresponding plurality of small-pixel detectors arranged directly in front of the large-pixel detector.

According to an exemplary embodiment, the first pixel detector further includes a first data collection board.

According to an exemplary embodiment, the second pixel detector further includes a second data collection board.

According to an exemplary embodiment, the system further includes a processing apparatus, wherein the processing apparatus is respectively connected to the first data collection board and the second data collection board, reads output signals of the first pixel detector array and the second pixel detector array, and acquires effective atomic number information of the to-be-detected object based on the output signals.

According to an exemplary embodiment, the ray source includes an X-ray source and an isotopic source.

According to an exemplary embodiment, the system further includes a reading circuit, relevant mechanical members, and the like auxiliary components.

The system according to the present disclosure is capable of improving the substance identification, space identification and penetration indicator at the same time. By parsing output signals of the low-energy small-pixel detector array arranged at the front and the high-energy large-pixel detector array arranged at the rear that have corresponding positions, the effective atomic number information of the to-be-detected object may be obtained. In addition, the small-pixel detectors arranged at the front have a good space identification function, which, in combination with the large-pixel detectors arranged at the rear, helps to improve the penetration.

Figure 5:
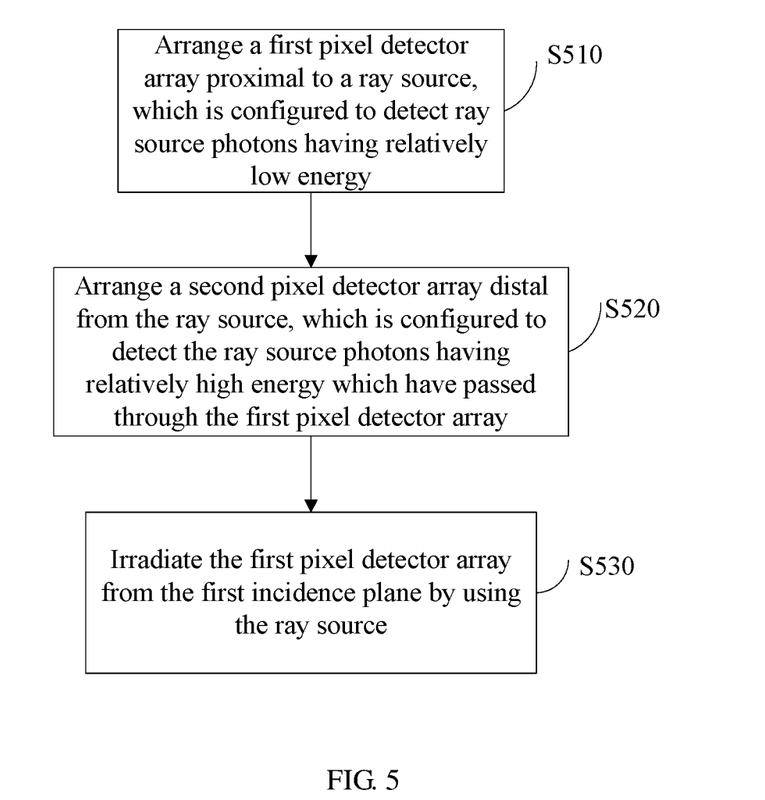
FIG. 5 schematically illustrates a flowchart of a dual-energy detection method according to an exemplary embodiment of the present disclosure.

FIG. 5 schematically illustrates a flowchart of a dual-energy detection method according to an exemplary embodiment of the present disclosure.

As illustrated in FIG. 5, in step S510, a first pixel detector array is arranged proximal to a ray source, which is configured to detect ray source photons having relatively low energy, wherein the first pixel detector array includes a plurality of rows of first pixel detectors, the first pixel detector including a first scintillator, a first photosensitive device, a first incidence plane for incidence of the ray source, and a first window coupled to the first photosensitive device, the first incidence plane facing towards the ray source.

In step S520, a second pixel detector array is arranged distal from the ray source, which is configured to detect the ray source photons having relatively high energy which have passed through the first pixel detector array, wherein the second pixel detector array includes a single row of second pixel detectors, the second pixel detector including a second scintillator, a second photosensitive device, a second incidence plane for incidence of the ray source, and a second window coupled to the second photosensitive device, each of the second pixel detectors having the same pixel area as corresponding plurality of first pixel detectors thereof.

In step S530, the first pixel detector array is irradiated from the first incidence plane by using the ray source.

According to an exemplary embodiment, the method further includes: reading output signals of the first pixel detector array and the second pixel detector array; and acquiring effective atomic number information of a to-be-detected object based on the output signals.

Other contents in this embodiment may be referenced to the contents described in other embodiments, which are thus not described herein any further.

FIG. 5 schematically illustrates a flowchart of a dual-energy detection method according to an exemplary embodiment of the present disclosure. The method, for example, may be implemented by using the dual-energy detection apparatus and system as illustrated in FIG. 1, FIG. 2, FIG. 3 or FIG. 4, which is not limited in the present disclosure. It should be noted that FIG. 5 only schematically illustrates, rather than limiting, the steps included in the method according to an exemplary embodiment of the present disclosure. It can be easily understood that, the steps as illustrated in FIG. 5 do not indicate or limit the time sequence of these steps. In addition, it can also be easily understood that, these steps may be performed, for example, in a plurality of modules/processes/threads synchronously or asynchronously.

Based on the above description of the embodiments, a person skilled in the art would easily understand that the method and corresponding modules according to the embodiments of the present disclosure may be implemented by means of software or partially hardening of the software. Based on such understandings, the technical solutions according to the embodiments of the present disclosure may be essentially embodied in the form of a software product. The software product may be stored in a non-volatile storage medium such as a CD-ROM, a U disk, a mobile hard disk and the like. The software product includes a number of instructions that enable a computer device (e.g., a PC, a server, a mobile terminal, a network device, or the like) to perform the methods provided in the embodiments of the present disclosure.

A person skilled in the art may understand that the accompanying drawings are only intended to schematically illustrate the exemplary embodiments, and the modules or procedures in the drawings are not necessarily included for implementing the present disclosure, which thus impose no limitation to the protection scope of the present disclosure.

A person skilled in the art would understand that the above modules may be arranged in the apparatus according to the description given in the embodiments, or may be subject to corresponding variations and arranged in one or a plurality of apparatuses different from that in the embodiments. The modules according to the above embodiments may be combined into one module, or may be split into a plurality of sub-modules.

Detailed above are exemplary embodiments of the present disclosure. It shall be understood that the present disclosure is not limited to the above exemplary embodiments. Instead, the present disclosure is intended to cover various modifications and equivalent deployments within the spirit and scope of the appended claims.

The invention claimed is:

1. A dual-energy detection apparatus, comprising:
   a first pixel detector array proximal to a ray source, configured to detect ray source photons having relatively low energy; and
   a second pixel detector array distal from the ray source, configured to detect the ray source photons having relatively high energy which have passed through the first pixel detector array;
   wherein the first pixel detector array comprises a plurality of rows of first pixel detectors, an amount of the first pixel detectors in each row is identical and the first pixel detectors at corresponding positions are aligned, the first pixel detector comprising a first sensitive medium, a first photosensitive device, a first incidence plane for incidence of the ray source, and a first window coupled to the first photosensitive device, the first incidence plane facing towards the ray source;
   wherein the second pixel detector array comprises a single row of second pixel detectors, the second pixel detector comprising a second sensitive medium, a second photosensitive device, a second incidence plane for incidence of the ray source, and a second window coupled to the second photosensitive device;
   wherein each of the second pixel detectors has the same pixel area as corresponding plurality of first pixel detectors thereof;
   wherein the first sensitive medium is a first scintillator; each of the first pixel detectors comprises the first scintillator having a rectangular shape and a first reflection layer coating the first scintillator, the first reflection layer exposing the first window; and one side of each of the first pixel detectors opposite to the first window is the first incidence plane; and
   wherein the first pixel detector array and the second pixel detector array are configured to detect megavolt-level ray source photons, and lateral sizes and secondary electron ranges of the first pixel detectors are identical.

2. The apparatus according to claim 1, wherein the second sensitive medium is a second scintillator; and each of the second pixel detectors comprises the second scintillator having a rectangular shape and a second reflection layer coating the second scintillator, the second reflection layer exposing the second window.

3. The apparatus according to claim 1, wherein the first pixel detector further comprises a first data collection board.

4. The apparatus according to claim 1, wherein the second pixel detector further comprises a second data collection board.

5. The apparatus according to claim 1, wherein the ray source comprises an X-ray source and an isotopic source.

6. The apparatus according to claim 1, wherein a mass thickness of the first pixel detector is determined based on any one or any combination of the type of the ray source, the type of the first sensitive medium and the size of the pixel.

7. The apparatus according to claim 6, wherein a mass thickness of the second pixel detector is selected such that the second pixel detector array is capable of effectively detecting the ray source photons having relatively high energy, and the mass thickness of the second pixel detector is greater than the mass thickness of the first pixel detector.

8. A dual-energy detection system, comprising:
   a ray source located on one side of a to-be-detected object; and
   a dual-energy detection apparatus located on the other side of the to-be-detected object;
   wherein the dual-energy detection apparatus comprises:
      a first pixel detector array proximal to the ray source, configured to detect ray source photons having relatively low energy; and
      a second pixel detector array distal from the ray source, configured to detect the ray source photons having relatively high energy which have passed through the first pixel detector array;
      wherein the first pixel detector array comprises a plurality of rows of first pixel detectors, an amount of the first pixel detectors in each row is identical and the first pixel detectors at corresponding positions are aligned, the first pixel detector comprising a first sensitive medium, a first photosensitive device, a first incidence plane for incidence of the ray source, and a first window coupled to the first photosensitive device, the first incidence plane facing towards the ray source;
      the second pixel detector array comprises a single row of second pixel detectors, the second pixel detector comprising a second sensitive medium, a second photosensitive device, a second incidence plane for incidence of the ray source, and a second window coupled to the second photosensitive device; and
      each of the second pixel detectors has the same pixel area as corresponding plurality of first pixel detectors thereof,
   wherein the first sensitive medium is a first scintillator; each of the first pixel detectors comprises the first scintillator having a rectangular shape and a first reflection layer coating the first scintillator, the first reflection layer exposing the first window; and one side of each of the first pixel detectors opposite to the first window is the first incidence plane, and
   wherein the first pixel detector array and the second pixel detector array are configured to detect megavolt-level ray source photons, and lateral sizes and secondary electron ranges of the first pixel detectors are identical.

9. The system according to claim 8, wherein the first pixel detector further comprises a first data collection board.

10. The system according to claim 9, wherein the second pixel detector further comprises a second data collection board.

11. The system according to claim 10, further comprising a processing apparatus, wherein the processing apparatus is respectively connected to the first data collection board and the second data collection board, reads output signals of the first pixel detector array and the second pixel detector array, and acquires effective atomic number information of the to-be-detected object based on the output signals.

12. The system according to claim 8, wherein the ray source comprises an X-ray source and an isotopic source.

13. A dual-energy detection method, comprising:
   arranging a first pixel detector array proximal to a ray source, which is configured to detect ray source photons having relatively low energy, wherein the first pixel detector array comprises a plurality of rows of first pixel detectors, an amount of the first pixel detectors in each row is identical and the first pixel detectors at corresponding positions are aligned, the first pixel detector comprising a first scintillator, a first photosensitive device, a first incidence plane for incidence of the ray source, and a first window coupled to the first photosensitive device, the first incidence plane facing towards the ray source;
   arranging a second pixel detector array distal from the ray source, which is configured to detect the ray source photons having relatively high energy which have passed through the first pixel detector array, wherein the second pixel detector array comprises a single row of second pixel detectors, the second pixel detector comprising a second scintillator, a second photosensitive device, a second incidence plane for incidence of the ray source, and a second window coupled to the second photosensitive device, each of the second pixel detectors having the same pixel area as corresponding plurality of first pixel detectors thereof; and irradiating the first pixel detector array from the first incidence plane by using the ray source, wherein the first sensitive medium is a first scintillator; each of the first pixel detectors comprises the first scintillator having a rectangular shape and a first reflection layer coating the first scintillator, the first reflection layer exposing the first window; and one side of each of the first pixel detectors opposite to the first window is the first incidence plane, and wherein the first pixel detector array and the second pixel detector array are configured to detect megavolt-level ray source photons, and lateral sizes and secondary electron ranges of the first pixel detectors are identical.

14. The method according to claim 13, further comprising:

reading output signals of the first pixel detector array and the second pixel detector array; and acquiring effective atomic number information of a to-be-detected object based on the output signals.

\* \* \* \* \*